United States Patent
Kilemnik

(10) Patent No.: US 12,268,411 B2
(45) Date of Patent: Apr. 8, 2025

(54) RADIAL CUTTER IMPLANT

(71) Applicant: Medi-Tate Ltd., Or Akiva (IL)

(72) Inventor: Ido Kilemnik, Haniel (IL)

(73) Assignee: MEDI-TATE LTD., Or Akiva (IL)

( * ) Notice: Subject to any disclaimer, the term of this patent is extended or adjusted under 35 U.S.C. 154(b) by 0 days.

(21) Appl. No.: 18/329,470

(22) Filed: Jun. 5, 2023

(65) Prior Publication Data

US 2023/0310024 A1 Oct. 5, 2023

Related U.S. Application Data

(63) Continuation of application No. 15/782,754, filed on Oct. 12, 2017, now Pat. No. 11,969,183, which is a
(Continued)

(51) Int. Cl.
*A61B 17/3207* (2006.01)
*A61F 2/94* (2013.01)
(Continued)

(52) U.S. Cl.
CPC ........ *A61B 17/320725* (2013.01); *A61F 2/94* (2013.01); *A61B 2017/00274* (2013.01);
(Continued)

(58) Field of Classification Search
CPC ........ A61B 17/3207; A61B 17/320725; A61B 17/320733; A61B 2017/32096; A61B 2017/00274
See application file for complete search history.

(56) References Cited

U.S. PATENT DOCUMENTS 4,425,908 A 1/1984 Simon
5,209,725 A 5/1993 Roth
(Continued)

FOREIGN PATENT DOCUMENTS

WO WO 2004/078065 A2 9/2004
WO 2006040767 A1 4/2006
(Continued)

OTHER PUBLICATIONS

Indian First Examination Report received for Indian Application No. 202148014965 on Mar. 9, 2023, 6 pgs.
(Continued)

*Primary Examiner* — Todd J Scherbel
(74) *Attorney, Agent, or Firm* — Merchant & Gould P.C.

(57) ABSTRACT

A method for expanding a constricted location of a urethra of a subject, the method including inserting a urethral implant, and an implant sheath that covers the urethral implant, through the urethra for implanting the urethral implant in the constricted location, the urethral implant being in a compressed configuration within the implant sheath, releasing the urethral implant from the implant sheath until the urethral implant exits from the implant sheath, thereby expanding the urethral implant from the compressed configuration to an expanded configuration, applying, by the urethral implant, continuous pressure on tissues of the urethra at the constricted location, and retracting the implant sheath from the urethra.

10 Claims, 15 Drawing Sheets

Related U.S. Application Data continuation of application No. 13/141,307, filed as application No. PCT/IL2009/001207 on Dec. 22, 2009, now Pat. No. 9,848,905.

(60) Provisional application No. 61/288,426, filed on Dec. 21, 2009, provisional application No. 61/139,718, filed on Dec. 22, 2008.

(51) Int. Cl.
| | |
|---|---|
| *A61B 17/00* | (2006.01) |
| *A61B 17/29* | (2006.01) |
| *A61B 17/3209* | (2006.01) |
| *A61B 18/00* | (2006.01) |
| *A61F 2/04* | (2013.01) |

(52) U.S. Cl.
CPC .......... *A61B 2017/2945* (2013.01); *A61B 2017/32096* (2013.01); *A61B 2018/00547* (2013.01); *A61F 2002/048* (2013.01); *A61F 2220/0016* (2013.01); *A61F 2230/0058* (2013.01); *A61F 2230/006* (2013.01); *A61F 2230/0076* (2013.01); *A61F 2250/0059* (2013.01)

(56) References Cited

U.S. PATENT DOCUMENTS

| | | | |
|---|---|---|---|
| 5,499,994 | A | 3/1996 | Tihon et al. |
| 5,601,591 | A | 2/1997 | Edwards et al. |
| 6,491,672 | B2 | 10/2002 | Slepian |
| 6,508,833 | B2 | 1/2003 | Pavcnik et al. |
| 7,179,275 | B2 | 2/2007 | McGuckin et al. |
| 7,803,171 | B1 | 9/2010 | Uflacker |
| 7,837,610 | B2 | 11/2010 | Lichtenstein et al. |
| 8,062,326 | B2 | 11/2011 | McGuckin et al. |
| 8,308,752 | B2 | 11/2012 | Tekulve |
| 9,005,242 | B2 | 4/2015 | Cahill |
| 9,848,905 | B2 * | 12/2017 | Kilemnik ....... A61B 17/320725 |
| 2001/0011187 | A1 | 8/2001 | Pavcnik |
| 2003/0114877 | A1 | 6/2003 | Gellman |
| 2005/0015129 | A1 | 1/2005 | Mische |
| 2005/0273135 | A1 | 12/2005 | Chanduszko |
| 2006/0025800 | A1 | 2/2006 | Suresh |
| 2006/0095058 | A1 | 5/2006 | Sivan et al. |
| 2006/0235463 | A1 | 10/2006 | Freudenthal |
| 2008/0275494 | A1 | 11/2008 | Fleming |
| 2008/0300594 | A1 | 12/2008 | Goto |
| 2009/0069828 | A1 | 3/2009 | Martin |
| 2009/0069840 | A1 | 3/2009 | Hallisey |
| 2009/0276048 | A1 | 11/2009 | Chirico et al. |
| 2010/0137893 | A1 | 6/2010 | Kilemnick et al. |
| 2018/0318114 | A1 | 11/2018 | Huang |

FOREIGN PATENT DOCUMENTS

| | | |
|---|---|---|
| WO | WO 2008/136005 A2 | 11/2008 |
| WO | WO 2010/073244 A9 | 6/2010 |

OTHER PUBLICATIONS

Extended European Search Report received for EP Application No. 23000113.3 on Nov. 24, 2023, 9 pgs.

* cited by examiner

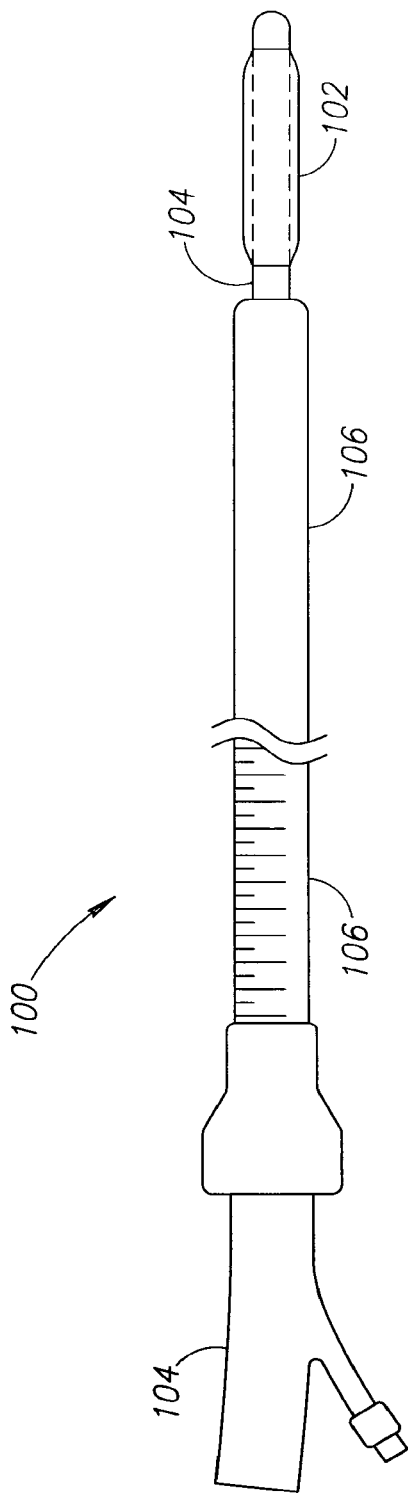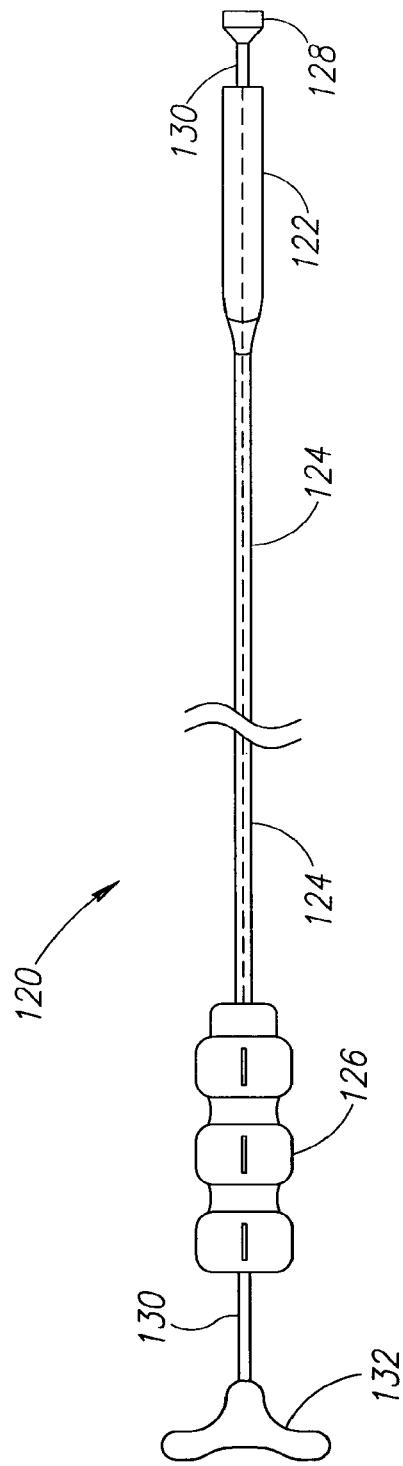
FIG.1
FIG.2

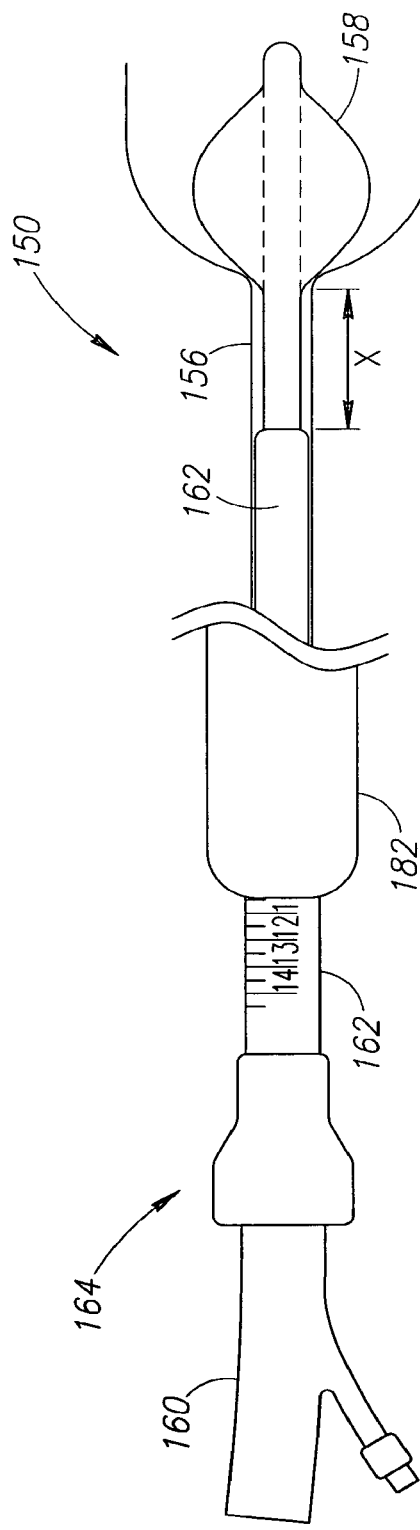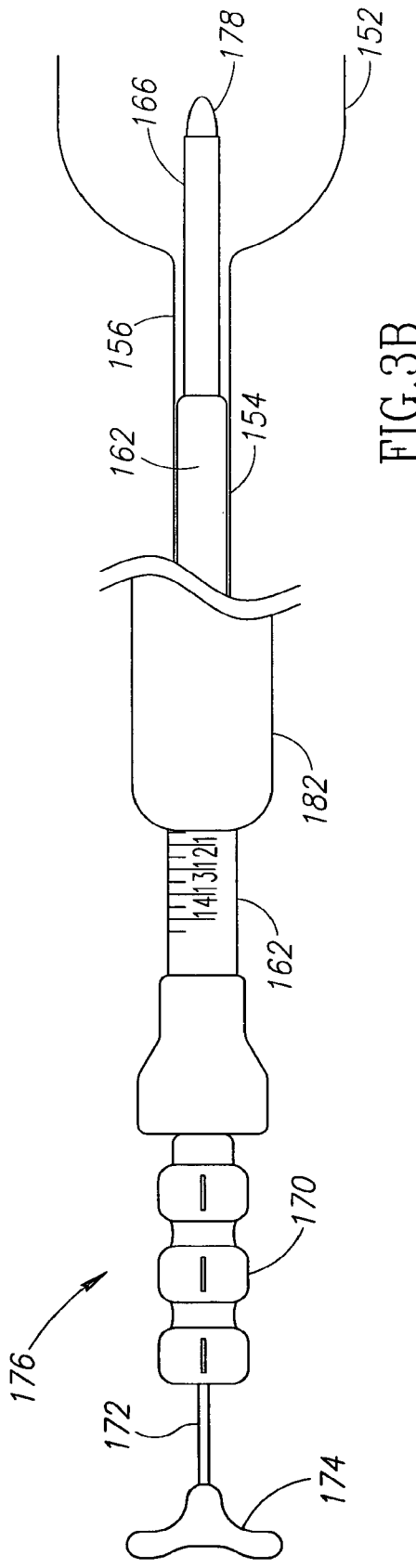
FIG.3A
FIG.3B

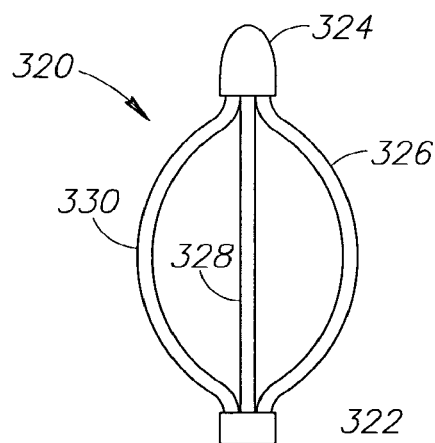
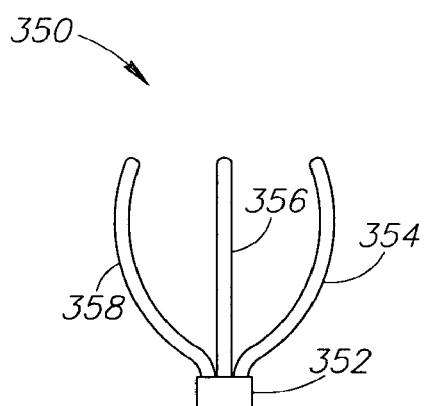
FIG.6A          FIG.7A
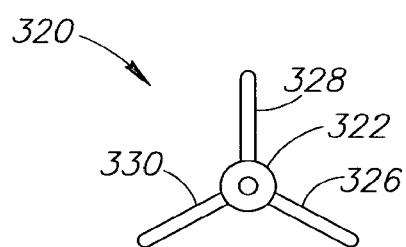
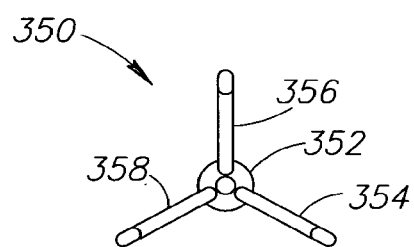
FIG.6B          FIG.7B
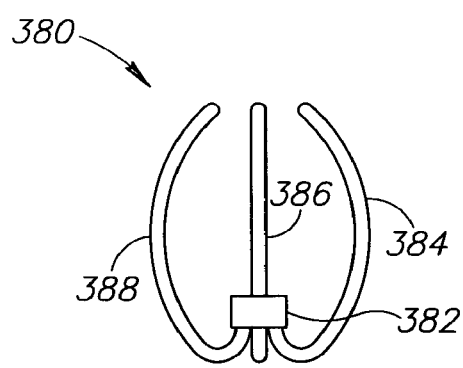
FIG.8

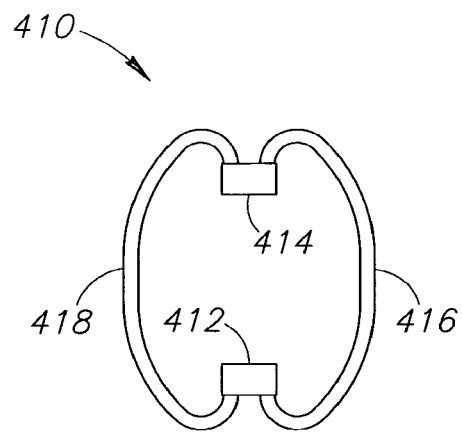
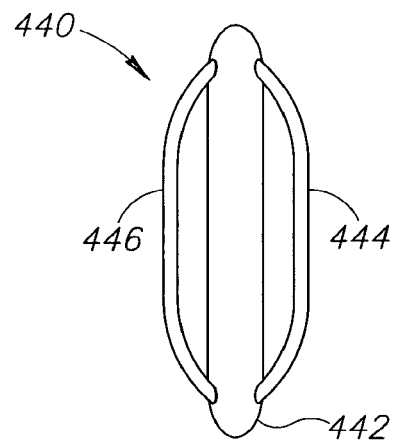
FIG.9A
FIG.10A
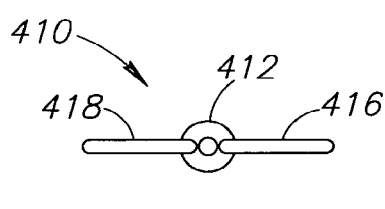
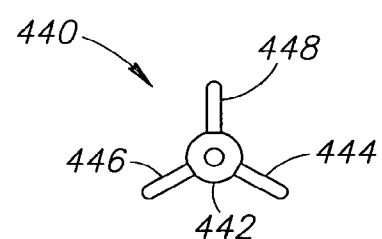
FIG.9B
FIG.10B

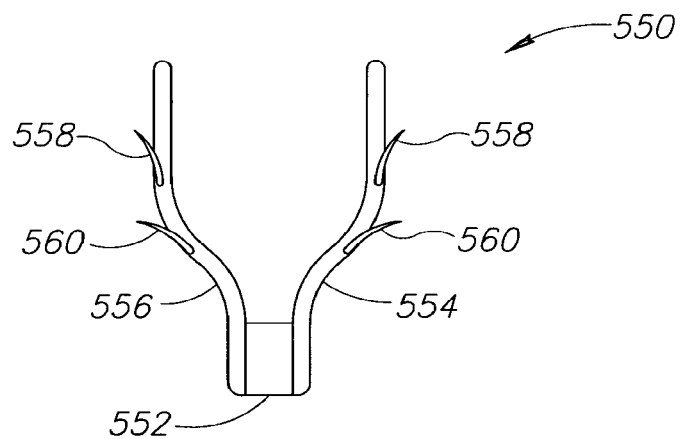
FIG.14
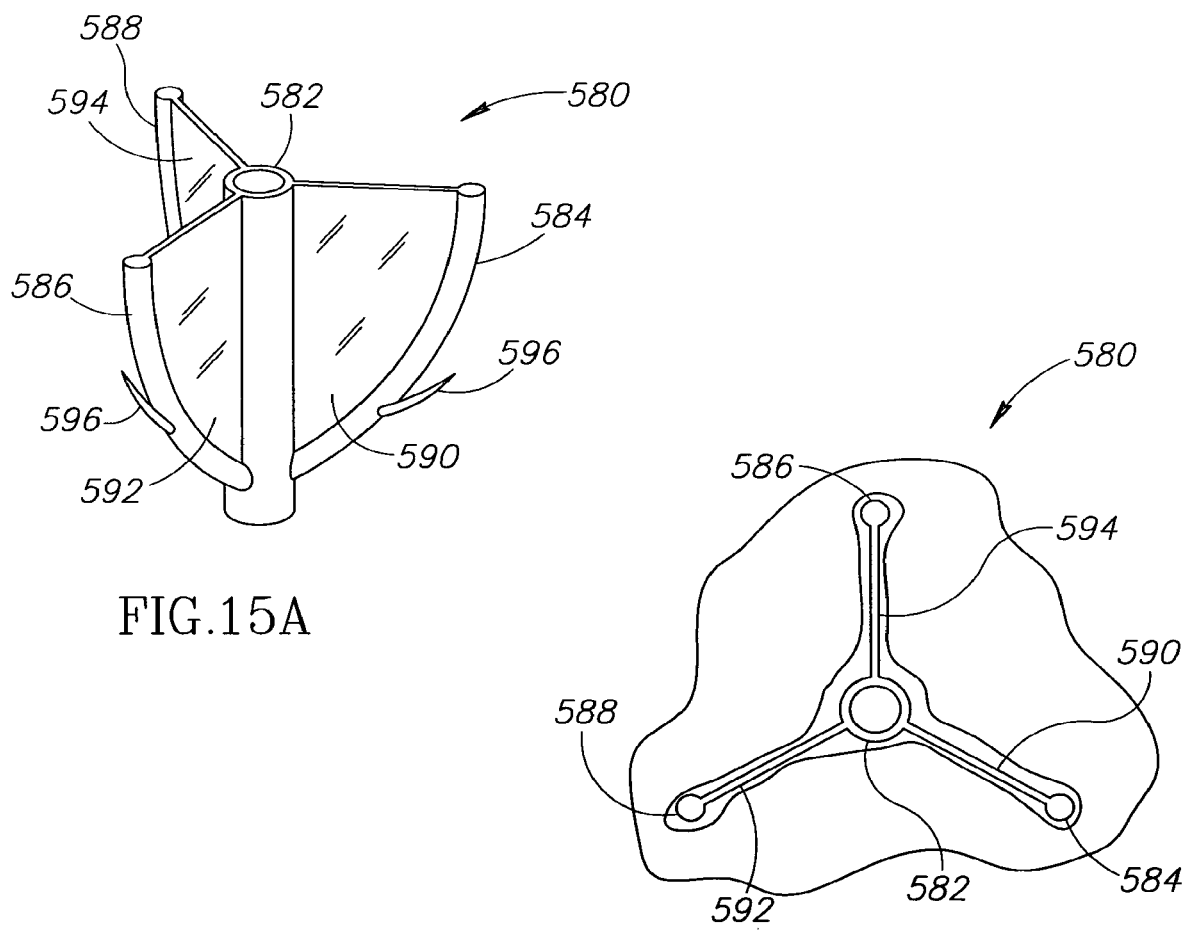
FIG.15A
FIG.15B

RADIAL CUTTER IMPLANT

CROSS-REFERENCE TO RELATED APPLICATIONS

This application is a continuation of U.S. application Ser. No. 15/782,754, filed Oct. 12, 2017, which is a continuation of U.S. application Ser. No. 13/141,307, filed Jul. 28, 2011, which is a National Stage Application of PCT/IL2009/001207, filed Dec. 22, 2009, which claims benefit of U.S. Provisional Application No. 61/288,426, filed Dec. 21, 2009 and U.S. Provisional Application No. 61/139,718, filed Dec. 22, 2008, which applications are incorporated herein by reference. To the extent appropriate, a claim of priority is made to the above disclosed applications.

FIELD OF THE DISCLOSED TECHNIQUE

The disclosed technique relates to system and method for treating a prostate enlargement (e.g., as a result of benign prostatic hyperplasia), in general, and to systems and methods for creating incisions in the muscles of the bladder neck, in particular.

BACKGROUND OF THE DISCLOSED TECHNIQUE

The prostate is a walnut-sized gland that forms part of the male reproductive system. The prostate is located in front of the rectum and just below the bladder, where urine is stored. The prostate surrounds the urethra, the canal through which urine passes out of the body. Prostate enlargement can result from a number of medical problems such as Benign Prostatic Hyperplasia (BPH), prostatic Bladder Neck Obstruction (BNO) and the like. The enlarged prostate applies pressure on the urethra and damages bladder function.

Transurethral incision of the prostate (TUIP) is an endoscopic procedure usually performed under general anaesthetic in which a surgeon employs an instrument (e.g., a scalpel, a laser beam generator and an electrical current actuator) inserted into the urethra for making incisions in the bladder neck where the prostate meets the bladder (i.e., more specifically in the midline to the level of the verumontanum). Incising the muscles in the bladder neck area relieves the obstructive effect of the prostate on the bladder neck and prostatic urethra and relaxes the opening of the bladder, thus decreasing resistance to the flow of urine out of the bladder. It is noted that, no tissue is removed during TUIP.

Infarction is a process resulting in a macroscopic area of necrotic tissue in some organ caused by loss of adequate blood supply. The inadequate blood supply can result from pressure applied to the blood vessels. Even by applying a relative small but continuous pressure on a tissue, one can block the tiny blood vessels within the tissue and induce infarction.

PCT patent application publication No. WO 2006/040767 A1 to the inventor, entitled "Prostate Treatment Stent" is directed at a tissue dissecting implant kit. The tissue dissecting implant kit includes an implant and a sterile package. The implant includes a plurality of rings elastically coupled there-between. An elastic pressure is applied on tissue caught between adjacent rings. The sterile package encompasses the implant. The implant has different distances between adjacent rings along its length. Alternatively, the implant has different material thickness or cross-section shape along its length. It is noted that, the tissue dissecting implant kit applies pressure on tissue caught between adjacent rings until the tissue is cut away or until the tissue falls off.

U.S. Pat. No. 5,209,725 issued to Roth, and entitled "Prostatic Urethra Dilatation Catheter System and Method", is directed to an instrument for performing a transurethral balloon dilatation procedure of the prostate. The balloon dilatation instrument includes a hollow catheter and optical viewing means. The hollow catheter includes a shaft, an inflatable optically transparent balloon, and at least one suitable visible marking.

The distal end portion of the shaft is made of an optically transparent material. The inflatable optically transparent balloon is coupled with the distal end portion of the shaft, and is sized to dilate the prostatic urethra. The at least one suitable visible marking is positioned on the catheter proximally to the balloon, such that the marking can be visualized relative to a predetermined anatomical landmark (e.g., verumon tanum). In this manner, proper positioning of the balloon, relative to the prostatic urethra, is performed prior to and during the dilation of the prostatic urethra. The optical viewing means is slidable within the catheter, for visibly viewing the marking intra-luminally from within the catheter. The balloon is correctly located relative to the prostatic urethra. The balloon is inflated so as to dilate the prostatic urethra without damaging the external sphincter at the apex of the prostate.

U.S. Pat. No. 5,499,994 issued to Tihon et al., and entitled "Dilation Device for the Urethra", is directed to a dilation device for opening a portion of an obstructed urethra. The dilation device includes an inner hollow tubular core and an outer confining covering. The inner hollow tubular core defines a lumen therein. The lumen is a conduit of sufficient diameter to permit urine to flow freely there-through from the bladder. The core is substantially non-collapsible. The outer confining covering is capable of expanding radially outwardly to a predetermined extent. The covering has a length of at least partially that of the obstructed portion of the urethra. The dilation device can further include retractable spikes for anchoring the device in its intended position.

SUMMARY OF THE PRESENT DISCLOSED TECHNIQUE

It is an object of the disclosed technique to provide a novel method and system for creating incisions in the muscles of the bladder neck by implanting a radial cutter implant which applies continuous pressure on the muscles of the bladder neck.

In accordance with the disclosed technique, there is thus provided an implant for creating incisions in the tissues surrounding the bladder neck and the urethra of a patient, for relaxing the opening of the bladder. The implant includes a central connector and at least one wire. The wires extend radially outwardly from the center of the central connector. The wires apply continuous pressure on the surrounding tissues. The wires are foldable within an implant sheath for enabling delivery and extraction thereof. The implant is implanted within a restricted location of the urethra for a period of time for creating incisions at the locations where the wires apply pressure on the surrounding tissues.

In accordance with another embodiment of the disclosed technique, there is thus provided a method for creating incisions in the tissues surrounding the bladder neck and the urethra of a patient for relaxing the opening of the bladder. The method includes the procedures of delivering a radial cutter implant, releasing the radial cutter, applying continuous pressure, and extracting the radial cutter implant. The radial cutter implant is delivered to a constricted location within the urethra by employing a delivery system. After the radial cutter implant is delivered the delivery system is removed. The continuous pressure is applied on the surrounding tissues by employing the radial cutter implant. At the appearance of a predetermined condition, the radial cutter implant is extracted from the patient.

In accordance with a further embodiment of the disclosed technique, there is thus provided a delivery system for delivering a radial cutter implant. The delivery system includes a positioning tube, a balloon tube, a balloon, an internal delivery tube, and an implant sheath. The balloon tube slidably goes through the portioning tube. The balloon is coupled with a distal end of the balloon tube. The balloon is inflatable via the balloon tube. The radial cutter implant is coupled with a distal end of the internal delivery tube. The implant sheath is externally slidably coupled with the internal delivery tube for holding the radial cutter implant at a folded configuration during delivery and extraction thereof. A physician inserts the positioning tube and the balloon tube into a urethra of a patient until the balloon is positioned inside a bladder of the patient. The physician inflates the balloon and pulls the positioning tube and the balloon tube in the distal direction until the balloon is blocked by a bladder neck of the patient. The physician deflates the balloon. The physician removes the balloon tube while keeping the positioning tube in place. The physician inserts the internal delivery tube including the implant sheath, having the radial cutter implant folded therein. The physician positions the radial cutter implant within a constricted location of the urethra, according to the position of the positioning tube. The physician pulls the implant sheath and exposes the radial cutter implant. The radial cutter implant expands and applies pressure on surrounding tissues. The physician removes the internal delivery tube, including the implant sheath.

BRIEF DESCRIPTION OF THE DRAWINGS

The disclosed technique will be understood and appreciated more fully from the following detailed description taken in conjunction with the drawings in which:

FIG. 1 is a schematic illustration of an overtube for determining the location of a bladder neck of a patient and delivering a radial cutter implant thereto, constructed and operative in accordance with an embodiment of the disclosed technique;

FIG. 2 is a schematic illustration of a delivery for delivering a radial cutter implant to the bladder neck of a patient, constructed and operative in accordance with another embodiment of the disclosed technique;

FIGS. 3A, 3B and 3C are schematic illustrations of a system for delivering a radial cutter implant to the bladder neck of a patient, constructed and operative in accordance with a further embodiment of the disclosed technique;

FIGS. 6A and 6B are schematic illustrations of a radial cutter implant, constructed and operative in accordance with a further embodiment of the disclosed technique;

FIGS. 7A and 7B are schematic illustrations of a radial cutter implant, constructed and operative in accordance with another embodiment of the disclosed technique;

FIG. 8 is a schematic illustration of a radial cutter implant, constructed and operative in accordance with a further embodiment of the disclosed technique;

FIGS. 9A and 9B are schematic illustrations of a radial cutter implant, constructed and operative in accordance with another embodiment of the disclosed technique;

FIGS. 10A and 10B are schematic illustrations of a radial cutter implant, constructed and operative in accordance with a further embodiment of the disclosed technique;

FIG. 14 is a schematic illustration of radial cutter implant, constructed and operative in accordance with a further embodiment of the disclosed technique;

FIGS. 15A and 15B are schematic illustrations of a radial cutter implant, constructed and operative in accordance with another embodiment of the disclosed technique;

DETAILED DESCRIPTION OF THE EMBODIMENTS

Figure 3C:
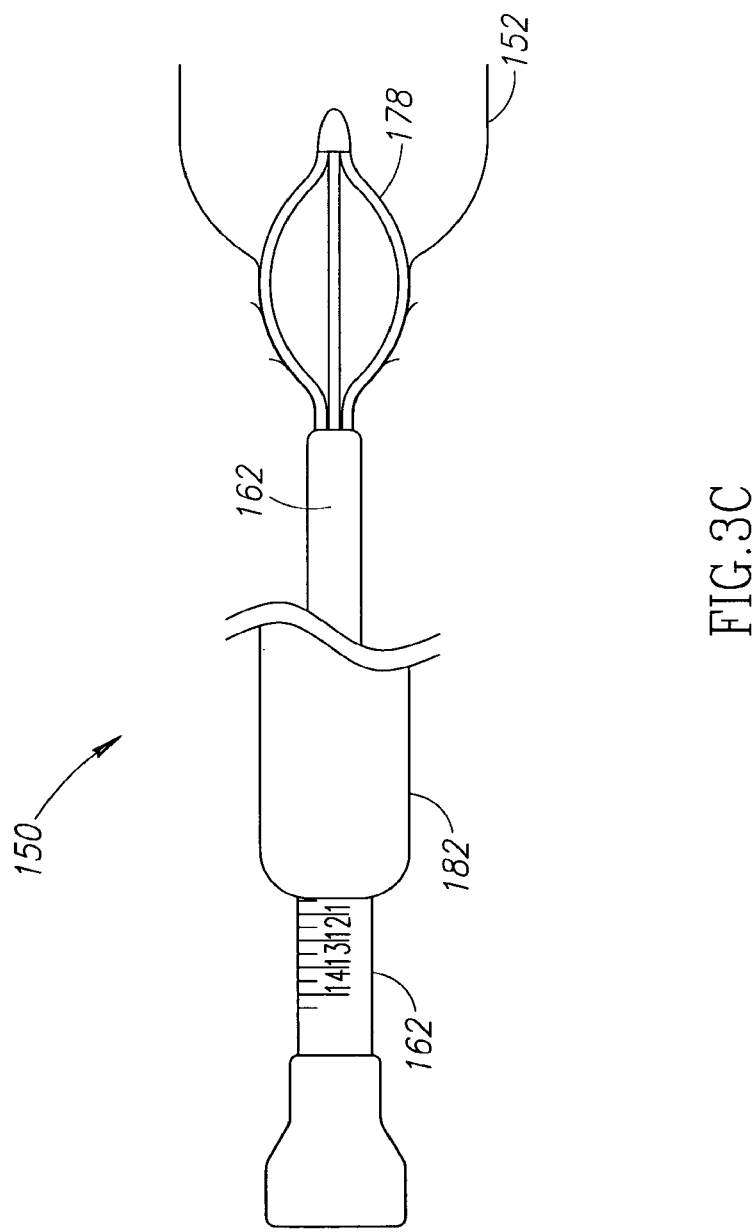

The disclosed technique overcomes the disadvantages of the prior art by providing an implant for applying small yet continuous pressure on the tissues of the bladder neck sphincter (i.e., as well as tissues of the urethra and the prostate gland) by a plurality of wires. The pressure induces infarction in the tissues (i.e., tissues of the bladder neck, urethra, and prostate gland) which creates a plurality of desired incisions (i.e., each of the wires creates an incision). The incisions relive a prostate enlargement problem by cutting through the tissues and extending the urinal passage (i.e., the wires both incise and extend the tissues in the radial direction from the urethra axis outwardly). The disclosed technique further includes a delivery and deployment system for the incising implant. It is noted that, in this application, a radial cutter implant which applies pressure on the tissues of the bladder neck, further applies pressure on the tissues of the prostate and urethra unless specifically mentioned otherwise along the text.

The terms proximal and distal refer to directions relative to the body of the patient. In particular, the term proximal refers to a direction facing toward the center of the body of the patient. The term distal refers to a direction facing the periphery of the body of the patient, opposite of the proximal direction. For example a catheter is inserted into the urethra of the patient with the proximal end thereof first.

Reference is now made to FIG. 1, which is a schematic illustration of an overtube, generally referenced 100, for determining the location of a bladder neck of a patient and delivering a radial cutter implant thereto, constructed and operative in accordance with an embodiment of the disclosed technique. Overtube 100 includes a balloon 102, a balloon tube 104 (i.e., balloon Foley-catheter 104), and a positioning tube 106. Balloon 102 is coupled around balloon tube 104. Balloon tube 104 slidably goes through positioning tube 106.

Overtube 100 enables a physician (not shown) to deploy a radial cutter implant (e.g., radial cutter implant 320 of FIG. 6A) at the bladder neck of a patient (both bladder neck and patient are not shown). The physician inserts overtube 100 through the urethra of the patient until balloon 102 is positioned within the bladder (e.g., bladder 152 of FIG. 3A) of the patient. The physician inflates balloon 102 via balloon tube 104. When balloon 102 is inflated, the physician pulls overtube 100 in the distal direction (i.e., the physician pulls overtube 100 back towards him) until inflated balloon 102 is blocked by the bladder neck. Thus, the physician determines the exact position of the bladder neck of the patient. The physician deflates balloon 102 and removes balloon tube 104 from overtube 100 while leaving positioning tube 106 in place. Alternatively, the physician can determine the location of the bladder neck, and position positioning tube 106 accordingly, by employing any method known in the art, such as Ureteroscopy, Ultra-Sound imaging, fluoroscopy, and the like.

Reference is now made to FIG. 2, which is a schematic illustration of a delivery system, generally referenced 120, for delivering a radial cutter implant to the bladder neck of a patient, constructed and operative in accordance with another embodiment of the disclosed technique. Delivery system 120 includes an implant sheath 122, an external tube 124, an external tube handle 126, an internal tube proximal end 128, an internal tube 130, and an internal tube handle 132. Implant sheath 122 is coupled with the proximal end of external tube 124. External tube handle 126 is coupled with the distal end of external tube 124. Internal tube proximal end 128 is coupled with the proximal end of internal tube 130. Internal tube 130 slidably goes through external tube 124. Internal tube handle 132 is coupled with the distal end of internal tube 130.

A radial cutter implant (not shown—e.g., radial cutter implant 320 of FIG. 6A) is detachably coupled with internal tube proximal end 128 such that the implant is covered by implant sheath 122. In particular, and relating to the configuration of delivery system 120, as depicted in FIG. 2, internal tube 130 slides along external tube 124 in the distal direction until implant sheath 122 is positioned adjacent internal tube proximal end 128. In this manner implant sheath 122 covers the radial cutter implant, thereby restraining it.

The physician inserts delivery system 120 into the urethra of the patient through positioning tube 106 of FIG. 1. The physician employs positioning tube 106 (FIG. 1) for positioning the radial cutter implant at the location of the bladder neck (i.e., or of the restricted location of the urethra) as located by employing overtube 100. Once the radial cutter implant is positioned within the bladder neck, the physician exposes the radial cutter implant, as detailed further with reference to FIGS. 3A to 3C.

Reference is now made to FIGS. 3A, 3B and 3C which are schematic illustrations of a system, generally referenced 150, for delivering a radial cutter implant to the bladder neck of a patient, constructed and operative in accordance with a further embodiment of the disclosed technique. With reference to FIG. 3A, delivery system 150 includes an overtube 164, substantially similar to overtube 100 of FIG. 1. Overtube 164 includes a balloon 158, a balloon tube 160 and a positioning tube 162. Each of balloon 158, balloon tube 160 and positioning tube 162 is substantially similar to balloon 102, balloon tube 104 and positioning tube 106 of FIG. 1, respectively.

The physician inserts overtube 164 into a penis 182 of the patient and through a urethra 154 (FIG. 3B) of the patient, until balloon 158 is positioned within a bladder 152 of the patient. The physician inflates balloon 158 via balloon tube 160. Once balloon 158 is inflated, the physician pulls back overtube 164 (i.e., in the distal direction) until balloon 158 is blocked by bladder neck 156 of the patient. The physician deflates balloon 158 and removes balloon tube 160 from within overtube 164 while keeping positioning tube 162 in place. Thus, the physician locates the exact position of bladder neck 156.

With reference to FIG. 3B, delivery system 150 further includes a delivery 176, substantially similar to delivery system 120 of FIG. 2. Delivery 176 includes an implant sheath 166, an external tube 168 (located within positioning tube 162 and is not shown in the figure), an external tube handle 170, an internal tube 172, and an internal tube handle 174. Delivery system 150 further includes a radial cutter implant 178 within implant sheath 166. Each of implant sheath 166, external tube 168, external tube handle 170, internal tube 172, and internal tube handle 174, is substantially similar to each of implant sheath 122, external tube 124, external tube handle 126, internal tube 130, and internal tube handle 132, respectively.

After removing balloon tube 160 from overtube 164 (FIG. 3A), the physician inserts delivery 176 into positioning tube 162. The physician positions delivery 176 such that radial cutter implant 178 is positioned according to the position of positioning tube 162. The physician pulls external tube handle 170 for exposing radial cutter implant 178. Radial cutter implant 178 expands until it is attached to the walls of bladder neck 156 (i.e., to the muscles of bladder neck 156 and the surrounding tissues). Radial cutter implant 178 starts applying pressure to the walls of bladder neck 156 and urethra 154 (i.e., as well as on tissues of the prostate—not shown—as detailed herein above). In the example set forth in FIG. 3B, radial cutter implant 178 is self expanding. Alternatively, radial cutter implant 178 is expanded manually by the physician by employing an expander (i.e., a device for expanding implant 178 as known in the art—for example, a balloon).

With reference to FIG. 3C, radial cutter implant 178 is positioned within urethra 154 in an expanded configuration. The physician pulls positioning tube 162 out of the patient and leaves radial cutter implant within urethra 154 for a predetermined period of time (as detailed herein below— e.g., two weeks). Radial cutter implant 178 applies pressure on the walls of the surrounding tissues (e.g., bladder neck 156, urethra 154, and the prostate gland—not shown) incising the surrounding tissues over the predetermined period of time. The prolonged incision of the tissue, created by continuous pressure, decreases the pain involved in the procedure. Furthermore, by performing the incisions via continuous pressure (i.e., via infarction), bleeding is avoided.

The period of time, radial cutter implant 178 is implanted in the urethra of the patient, is determined by the physician at least according to the diagnosis of the patient (i.e., predetermined period of time). Alternatively, the time period is determined according to observations of the radial cutter implant effect over time (i.e., real time period determination), or any other way known in the art. Further alternatively, the time period ranges between one hour and twenty nine days.

Figure 4A:
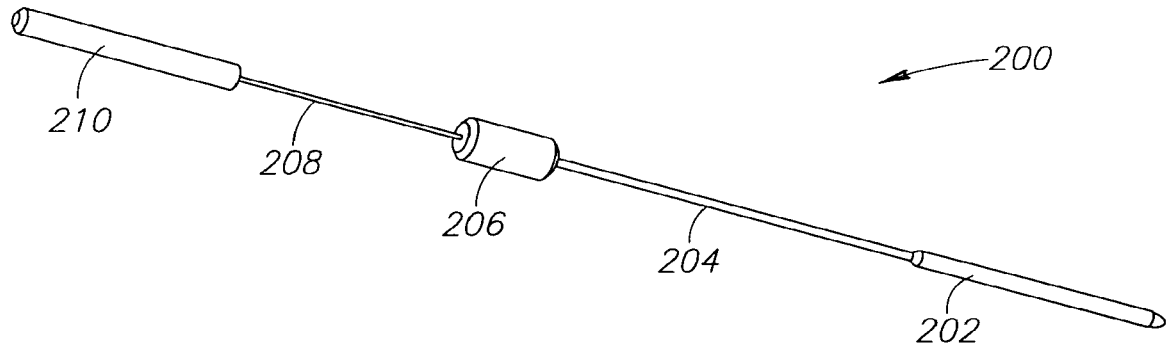
FIGS. 4A, 4B and 4C are schematic illustrations of a delivery for delivering a radial cutter implant, constructed and operative in accordance with another embodiment of the disclosed technique.
Figure 4B:
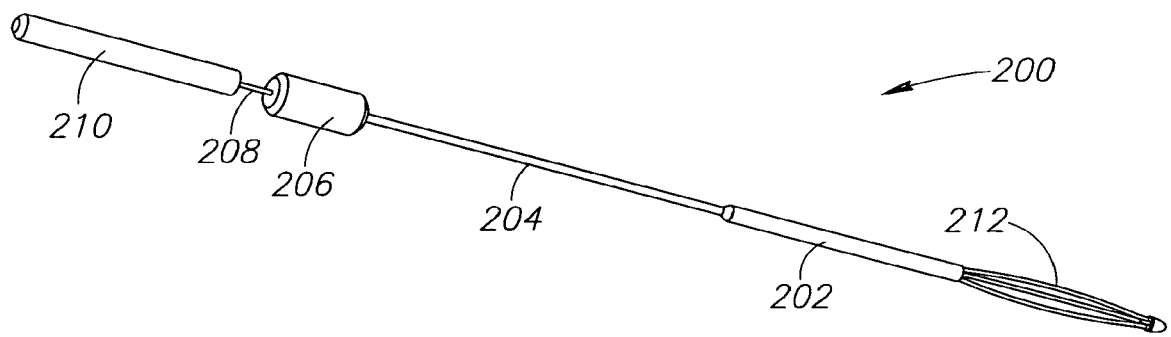
Figure 4C:
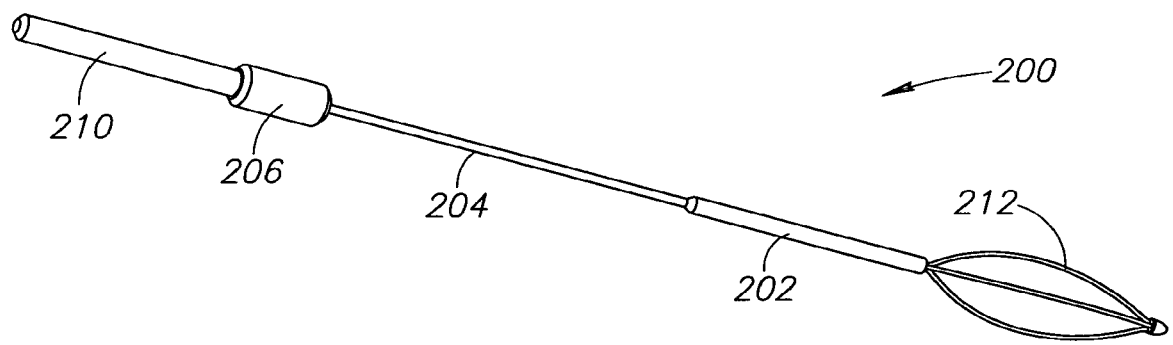

Reference is now made to FIGS. 4A, 4B and 4C, which are schematic illustrations of a delivery, generally referenced 200, for delivering a radial cutter implant, constructed and operative in accordance with another embodiment of the disclosed technique. With reference to FIG. 4A, delivery 200 is substantially similar to delivery system 120 of FIG. 2. Delivery 200 includes an implant sheath 202, an external tube 204, an external tube handle 206, an internal tube 208, and an internal tube handle 210. Each of implant sheath 202, external tube 204, external tube handle 206, internal tube 208, and internal tube handle 210 is substantially similar to each of implant sheath 122, external tube 124, external tube handle 126, internal tube 130, and internal tube handle 132 of FIG. 2, respectively.

Implant sheath 202 is coupled with the proximal end of external tube 204. External tube handle 206 is coupled with the distal end of external tube 204. A radial cutter implant 212 (FIG. 4B) is coupled, at a folded configuration thereof, with the proximal end of internal tube 208 and is covered by implant sheath 202. Internal tube 208 is slidably coupled with external tube 204. Internal tube handle 210 is coupled with the distal end of internal tube 208.

With reference to FIG. 4B, a physician (not shown) pulls external tube 204 via external tube handle 206 while keeping internal tube 208 in place. Thus, external tube 204 slides along internal tube 208 in the distal direction and implant sheath 202 is removed from radial cutter implant 212.

With reference to FIG. 4C, once implant sheath 202 is fully removed from radial cutter implant 212 (i.e., radial cutter implant is fully exposed), radial cutter implant 212 expands. In the example set forth in FIG. 4C, radial cutter implant 212 is self-expanding. Alternatively, radial cutter implant 212 is expanded manually by the physician employing an implant expander (not shown).

The physician leaves radial cutter implant 212 within the body of the patient for a predetermined period of time. When the physician wishes to remove radial cutter implant 212, the physician inserts delivery 200 into the urethra (not shown) of the patient. The physician couples the proximal end of internal tube 208 with radial cutter implant 212 by employing a coupler (not shown—e.g., coupler 240 of FIG. 5A). The physician pulls back internal tube 208 while keeping external tube 204 in place. Thus, radial cutter implant 212 is folded within, and is restrained by, implant sheath 202 and can be extracted from the body (i.e., the bladder neck and the urethra) of the patient, without damaging the tissues of the urethra. It is noted that, the delivery of radial cutter implant 212 and the extraction thereof are substantially a reveres duplicates of each other. In other words, the steps performed upon delivery are repeated in a reveres order upon extraction.

Figure 5A:
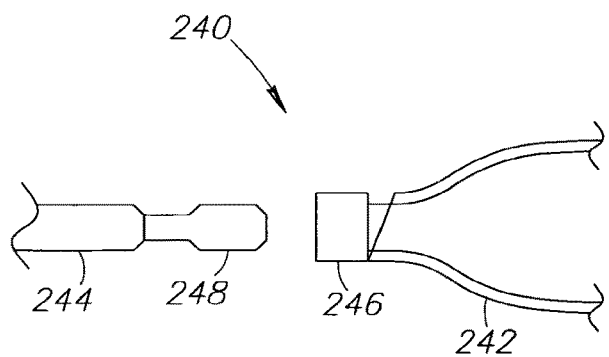
FIG. 5A is a schematic illustration of a coupler for coupling a radial cutter implant with an internal tube of a delivery system, constructed and operative in accordance with a further embodiment of the disclosed technique.
Figure 5B:
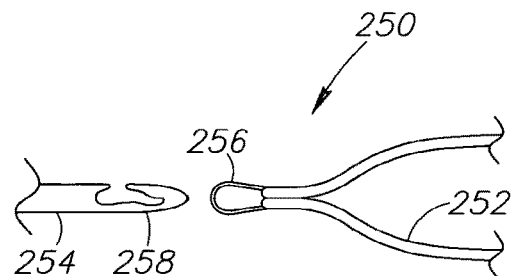
FIG. 5B is a schematic illustration of a coupler for coupling a radial cutter implant with an internal tube of a delivery system, constructed and operative in accordance with another embodiment of the disclosed technique.
Figure 5C:
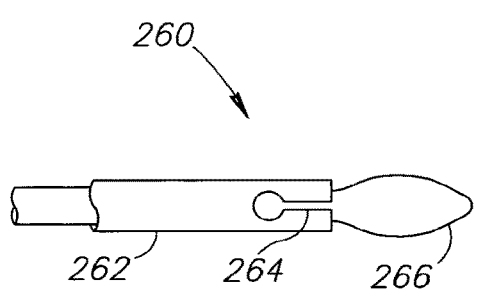
FIGS. 5C and 5D are schematic illustrations of a coupler for coupling a radial cutter implant with an internal tube of a delivery system, constructed and operative in accordance with a further embodiment of the disclosed technique.
Figure 5D:
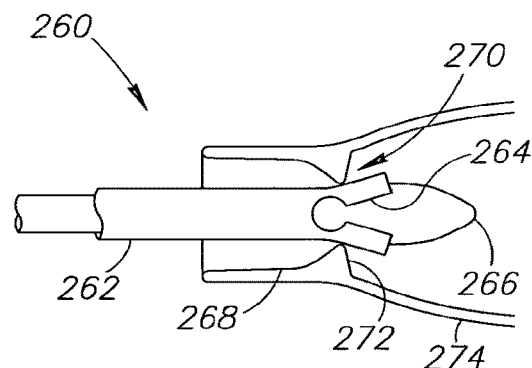
Figure 5E:
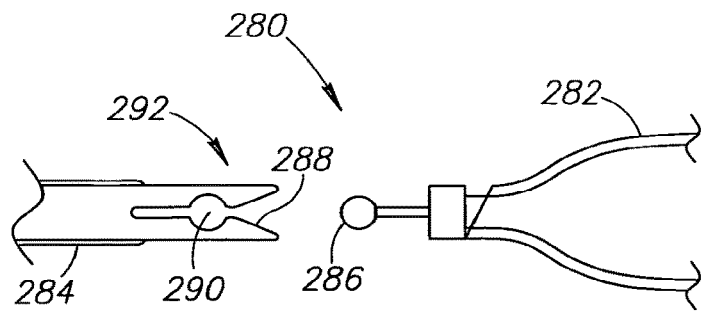
FIG. 5E is a schematic illustration of a coupler for coupling a radial cutter implant with an internal tube of a delivery system, constructed and operative in accordance with another embodiment of the disclosed technique.

Reference is now made to FIGS. 5A, 5B, 5C, 5D and 5E. FIG. 5A is a schematic illustration of a coupler, generally referenced 240, for coupling a radial cutter implant with an internal tube of a delivery system, constructed and operative in accordance with a further embodiment of the disclosed technique. FIG. 5B is a schematic illustration of a coupler, generally referenced 250, for coupling a radial cutter implant with an internal tube of a delivery system, constructed and operative in accordance with another embodiment of the disclosed technique. FIGS. 5C and 5D are schematic illustrations of a coupler, generally referenced 260, for coupling a radial cutter implant with an internal tube of a delivery system, constructed and operative in accordance with a further embodiment of the disclosed technique. FIG. 5E is a schematic illustration of a coupler, generally referenced 280, for coupling a radial cutter implant with an internal tube of a delivery system, constructed and operative in accordance with another embodiment of the disclosed technique.

With reference to FIG. 5A, coupler 240 includes a female portion 246 and a male portion 248. Male portion 248 is inserted into female portion 246 and is attached to female portion by screwing mechanism. In other words, the external circumference of male portion 248 is similar to that of a screw and the internal circumference of female portion 246 is similar to that of a nut. In the example set forth in FIG. 5A, female portion 246 is coupled with the distal end of a radial cutter implant 242 (e.g., radial cutter implant 320 of FIG. 6A), and male portion 248 is coupled with the proximal end of an internal tube 244 of a delivery system (e.g., internal tube 208 of FIG. 4A). Alternatively, female portion 246 is coupled with the proximal end of internal tube 244, and male portion 248 is coupled with the distal end of radial cutter implant 242.

With reference to FIG. 5B, coupler 250 includes a loop 256 and a hook 258. Hook 258 is inserted into loop 256 such that the physician is able to pull both hook 258 and loop 256 when pulling either of them. In the example set forth in FIG. 5B, loop 256 is coupled with the distal end of a radial cutter implant 252, and hook 258 is coupled with the proximal end of an internal tube 254. Alternatively, loop 256 is coupled with the proximal end of internal tube 254, and hook 258 is coupled with the distal end of radial cutter implant 252.

With reference to FIG. 5C, coupler 260 includes a dilating tip 266 and a recessed tube 262 (i.e., a tube which is sliced for forming a pair of pincers at the end thereof—the pincers are not referenced). Recessed tube 262 is coupled with the proximal end of a delivery system (e.g., delivery system 200 of FIG. 4A). Dilating tip 266 is coupled with recessed tube 262, such that dilating tip can be pulled into a recess 264 of recessed tube 262 and pushed out of recess 264 of recessed tube 262. When dilating tip 266 is positioned within recess 264, dilating tip 266 expands the diameter of recessed tube 262. Recessed tube 262 is coupled with the proximal end of an internal tube 262.

With reference to FIG. 5D, a distal end of a radial cutter implant 274 is coupled with a bottleneck 272. Bottleneck 272 includes an aperture 270 positioned approximately in the middle thereof. From the distal side of aperture 270 a gradually narrowing niche 268 is culminating in aperture 270. The diameter of aperture 270 is slightly larger than the diameter of recessed tube 260 and the diameter of dilating tip 266. The physician pushes dilating tip 266 and recessed tube 262 through aperture 270. After recessed tube 262 and dilating tip 266 are positioned proximally to aperture 270, the physician pulls dilating tip 266 into recess 264 for enlarging the diameter of recessed tube 262. When the physician pulls recessed tube 262 back in the distal direction, radial cutter implant 274 is pulled there-along (i.e., enlarged recessed tube 262 is blocked by aperture 270 of bottle neck 272). When the physician pushes dilating tip 266 away from recess 264, recessed tube 262 returns to the original diameter thereof. Thus, recessed tube 262 and dilating tip 266 can go through bottleneck 272 (i.e., through aperture 270).

In the example set forth in FIGS. 5C and 5D, recessed tube 262 and dilating tip 266 are coupled with an internal tube (not referenced) of the delivery system, and bottle neck 272 is coupled with a radial cutter implant 274. Alternatively, recessed tube 262 and dilating tip 266 are coupled with radial cutter implant 274, and bottleneck 272 is coupled with the internal tube.

With reference to FIG. 5E, coupler 280 includes a rigid ball 286 and a flexible socket 292. Flexible socket 292 includes a gradually narrowing opening 288 and a spherical niche 290. When rigid ball 286 is pushed against flexible socket 292, rigid ball 286 enters through gradually narrowing opening 288 and expands the proximal end thereof when entering spherical niche 290. Once rigid ball 286 is positioned inside flexible socket 290 (i.e., rigid ball 286 is securely coupled with flexible socket 292), the physician can pull flexible socket 292, and rigid ball 286 is pulled there-along. In the example set forth in FIG. 5E, rigid ball 286 is coupled with the distal end of a radial cutter implant 282, and flexible socket 292 is coupled with the proximal end of an internal tube 284. Alternatively, rigid ball 286 is coupled with the proximal end of internal tube 284, and flexible socket 292 is coupled with the distal end of radial cutter implant 282.

Reference is now made to FIGS. 6A and 6B, which are schematic illustrations of a radial cutter implant, generally referenced 320, constructed and operative in accordance with a further embodiment of the disclosed technique. With reference to FIG. 6A, radial cutter implant 320 is depicted from a side view perspective. Radial cutter implant 320 includes a distal end 322, three wires 326, 328 and 330, and a proximal end 324. Three wires 326, 328 and 330 are coupled between distal end 322 and proximal end 324. Distal end 322 is coupled with a coupler (e.g., coupler 240, 250, 260, and 280 of FIGS. 5A, 5B, 5C, and 5E, respectively).

Proximal end 324 is tapered for dilating the urethra of the patient during delivery of radial cutter implant 320. The shape of each of wires 326, 328 and 330, is substantially a portion of a circle. Each of wires 326, 328 and 330 is made from a Shape Memory Alloy (SMA), such as Nickel Titanium alloy (Nitinol). Alternatively, each of wires 326, 328 and 330 is made from any material which is flexible enough to be folded within an implant sheath and is strong enough (e.g., 0.5 Newton) to apply pressure on the surrounding tissues and induce infarction. Each of wires 326, 328 and 330 is flexible such that it can be straightened in order for radial cutter 320 to be folded within an implant sheath (e.g., implant sheath 202 of FIG. 4A—not shown). Each of wires 326, 328 and 330 springs back to the portion of the circle stance, once not limited by an obstacle (e.g., implant sheath 202 of FIG. 4A, the walls of the bladder neck of the patient). In this manner, when radial cutter implant 320 is positioned within the bladder neck of the patient, wires 326, 328 and 330, apply pressure to the surrounding tissues (e.g., bladder neck, urethra and prostate). With reference to FIG. 6B, radial cutter implant 320 is depicted from a bottom view perspective.

Alternatively, implant 320 is made of biodegradable materials, such that there is no need to remove implant 320 from the body of the patient. In this manner, implant 320 is constructed such it biodegrades, ceases from functioning and dissolves within the patient after the predetermined period of time, or after a triggering event initiated by the physician, as known in the art.

Reference is now made to FIGS. 7A and 7B, which are schematic illustrations of a radial cutter implant, generally referenced 350, constructed and operative in accordance with another embodiment of the disclosed technique. With reference to FIG. 7A, radial cutter implant 350 is depicted from a side view perspective. Radial cutter implant 350 includes a distal end 352 and three wires 354, 356, and 358. Each of distal end 352 and wires 354, 356, and 358, is substantially similar to each of distal end 322, and wires 326, 328, and 330 of FIG. 6A, respectively. Wires 354, 356, and 358 are not coupled there-between at the proximal end thereof. Radial cutter implant 350 operates in a substantially similar manner to that of radial cutter implant 320. With reference to FIG. 7B, radial cutter implant 350 is depicted from a bottom view perspective.

Reference is now made to FIG. 8, which is a schematic illustration of a radial cutter implant, generally referenced 380, constructed and operative in accordance with a further embodiment of the disclosed technique. Radial cutter implant 380 includes a distal end 382 and three wires 384, 386 and 388. Distal end 382 is substantially similar to distal end 322 of FIG. 6A. Each of wires 384, 386 and 388, is substantially similar to each of wires 326, 328 and 330 of FIG. 6A, respectively. Each of wires 384, 386 and 388 is in the shape of half a heart shape (i.e., the shape of a single side of a heart shape). Each of wires 384, 386 and 388 extends from the distal side of distal end 382 and U-turns to project proximally from distal end 382. In other words, each of wires 384, 386 and 388 is bent such that it is coupled with the distal side of distal end 382 and it extends proximally from distal end 382. Radial cutter implant 380 operates in a substantial similar manner to that of radial cutter implant 320 of FIG. 6A.

Reference is now made to FIGS. 9A and 9B, which are schematic illustrations of a radial cutter implant, generally referenced 410, constructed and operative in accordance with another embodiment of the disclosed technique. With reference to FIG. 9A, radial cutter implant 410 is depicted from a side view perspective. Radial cutter implant 410 includes a distal end 412, a proximal end 414 and two wires 416 and 418. Wires 416 and 418 are coupled between distal end 412 and proximal end 414. Distal end 412 is substantially similar to distal end 322 of FIG. 6A. Each of wires 416 and 418 is substantially similar to wire 326 of FIG. 6A. Each of wires 416 and 418 is coupled with the distal side of distal end 412 and with the proximal side of proximal end 414. Each of wires 416 and 418 is substantially C shaped. Radial cutter implant 410 operates in a substantial similar manner to that of radial cutter implant 320 of FIG. 6A. With reference to FIG. 9B, radial cutter implant 410 is depicted from a bottom view perspective.

Reference is now made to FIGS. 10A and 10B, which are schematic illustrations of a radial cutter implant, generally referenced 440, constructed and operative in accordance with a further embodiment of the disclosed technique. With reference to FIG. 10A, radial cutter implant 440 is depicted from a side view perspective. Radial cutter 440 includes a tube 442 and three wires 444, 446 and 448 (wire 448 is hidden behind tube 442 and is depicted in FIG. 10B).

Each of wires 444, 446 and 448 is substantially similar to each of wires 326, 328 and 330 of FIG. 6A. Each of wires 444, 446 and 448 is in the shape of a portion of a circle. The distal end of each of wires 444, 446 and 448 is coupled with the distal portion of tube 442, and the proximal end of each of wires 444, 446 and 448 is coupled with the proximal portion of tube 442. Tube 442 enables a clear passage of urine from the bladder of the patient through the bladder neck and into the urethra. The distal end of tube 442 can be coupled with an internal tube of a delivery system (e.g., delivery system 150 of FIGS. 3A to 3C) by employing a coupler (e.g., coupler 240 of FIG. 5A). Radial cutter implant 440 operates in a substantial similar manner to that of radial cutter implant 320. With reference to FIG. 10A, radial cutter implant 440 is depicted from a bottom view perspective.

Figure 11A:
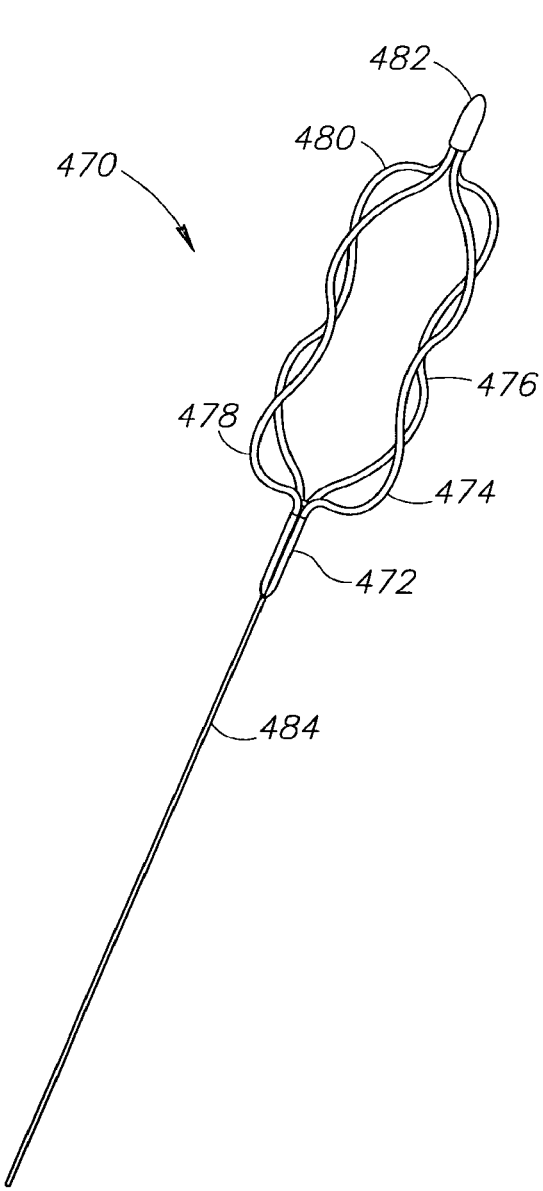
FIGS. 11A and 11B are schematic illustrations of a radial cutter implant, constructed and operative in accordance with another embodiment of the disclosed technique.
Figure 11B:
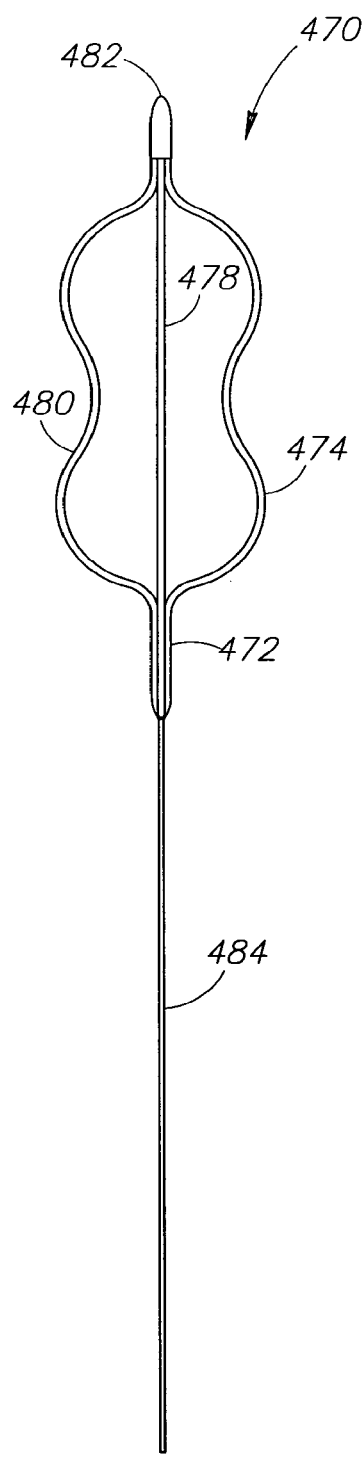

Reference is now made to FIGS. 11A and 11B, which are schematic illustrations of a radial cutter implant, generally referenced 470, constructed and operative in accordance with another embodiment of the disclosed technique. With reference to FIG. 11A, radial cutter implant 470 is depicted from an isometric perspective. Radial cutter implant 470 includes a distal end 472, four butterfly wing shaped wires 474, 476, 478 and 480, and a proximal end 482. Distal end 472 is substantially similar to distal end 322 of FIG. 6A. Proximal end 482 is substantially similar to proximal end 324 of FIG. 6A. Each of butterfly wing shaped wires 474, 476, 478 and 480 is coupled between distal end 472 and proximal end 482. Each of butterfly wing shaped wires 474, 476, 478 and 480 is flexible such that it can be folded within an implant sheath (e.g., implant sheath 402 of FIG. 4A).

The shape of each of butterfly wing shaped wires 474, 476, 478 and 480 enables radial cutter implant 470 to be fixed in the bladder neck of the patient without moving. Radial cutter implant 470 is narrower at the middle thereof than at the distal and proximal portions thereof (i.e., butterfly wing shaped wires 474, 476, 478 and 480). In this manner, the narrow middle of radial cutter implant 470 is positioned at the bladder neck of the patient. The proximal portion of radial cutter implant 470 is positioned within the bladder of the patient, and the distal portion of radial cutter implant 470 is positioned within the urethra of the patient, such that radial cutter implant 470 is fixed in place. A string 484 is looped around distal end 482 for enabling extraction of radial cutter implant 470. The physician (not shown) can employ the string 484 for guiding a delivery system (e.g., delivery system 150 of FIGS. 3A to 3C) for the extraction of radial cutter implant 470 (i.e., string 484 is employed as a guide wire). Radial cutter implant 470 operates in a substantially similar manner to that of radial cutter implant 322 of FIG. 6A. With reference to FIG. 11B, radial cutter implant 470 is depicted from a side view perspective.

Figure 12:
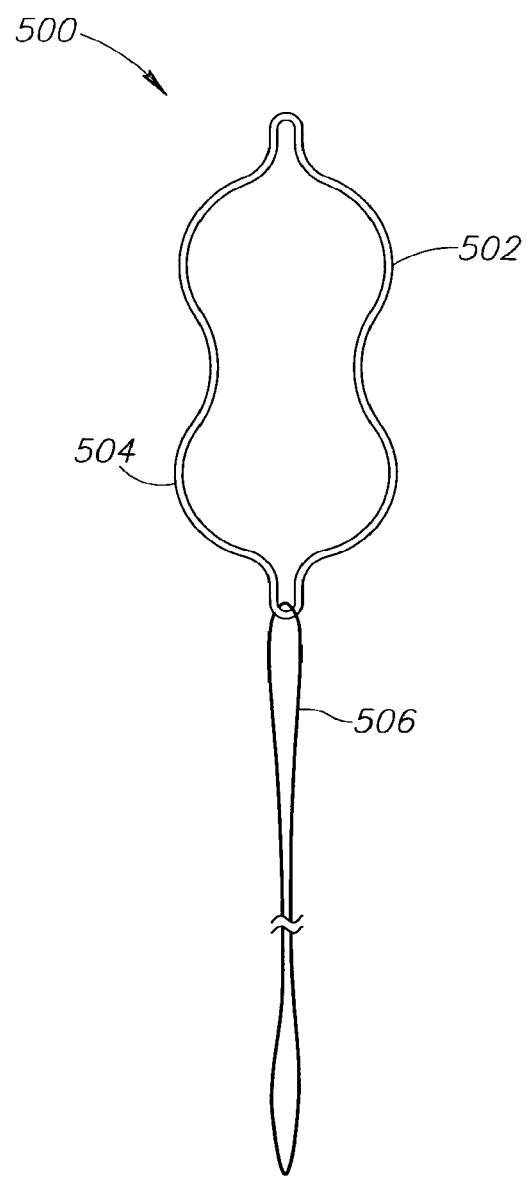
FIG. 12 is a schematic illustration of a radial cutter implant, constructed and operative in accordance with a further embodiment of the disclosed technique.

Reference is now made to FIG. 12, which is a schematic illustration of a radial cutter implant, generally referenced 500, constructed and operative in accordance with a further embodiment of the disclosed technique. Radial cutter implant 500 includes a right side portion 502 and a left side portion 504. Right side portion 502 is coupled with left side portion 504 at the proximal and distal ends thereof. Each of right side portion 502 and left side portion 504 is butterfly wing shaped. Each of right side portion 502 and left side portion 504 is substantially similar to butterfly wing shaped wire 474 of FIG. 11A. Radial cutter implant 500 is positioned in the bladder neck and is fixed in place in a substantial similar manner to that of radial cutter implant 470 of FIG. 11A. A string 506 is coupled with the distal end of radial cutter implant 500 for enabling extraction of radial cutter implant 500, for guiding a delivery system for the extraction procedure, or as anchoring device (i.e., string 506 is anchored outside of the body of the patient and prevents radial cutter implant 500 from moving).

In the examples set forth in FIGS. 6A, 6B, 7A, 7B, 8, 9A, 9B, 10A, 10B, 11A, 11B and 12, each of the radial cutter implants includes two to four wires. A radial cutter implant according to the disclosed technique should include at least one wire, radially extending outwardly from the center of the radial cutter implant, for applying pressure on the surrounding tissues. The radial cutter implant can include larger numbers of wires than four, such as five wires, six wires, and the like. The shape of the wires can be a portion of a circle, a butterfly wing shape, a polygon, and the like. The cross-section of the wires is round, rectangular, triangular, or any polygonal shaped.

In the examples set forth in FIGS. 6A, 6B, 7A, 7B, 8, 9A, 9B, 10A, 10B, 11A, 11B and 12, each of the radial cutters include either a distal end or a tube coupled with the distal end of the wires. It is noted that, a radial cutter implant according to the disclosed technique includes at least one central connector (e.g., distal end 322 of FIG. 6A or tube 442 of FIG. 10A) connecting the wires. It is further noted that the central connector can be connected to the wires at the proximal end of the wires, at the distal end of the wires, and at any point in the middle of the wires.

Figures 13A, 13B:
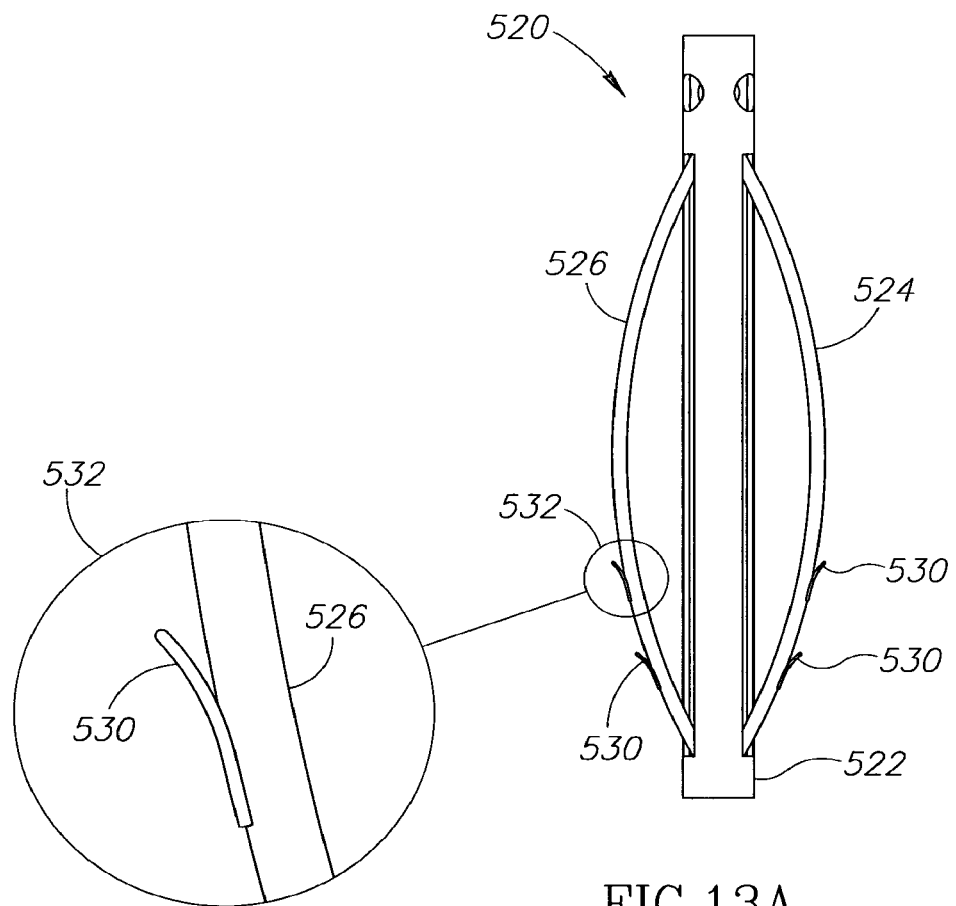
FIGS. 13A, 13B and 13C are schematic illustrations of a radial cutter implant, constructed and operative in accordance with another embodiment of the disclosed technique.
Figure 13C:
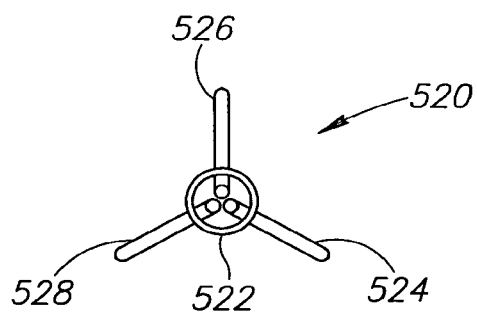
Figure 16A:
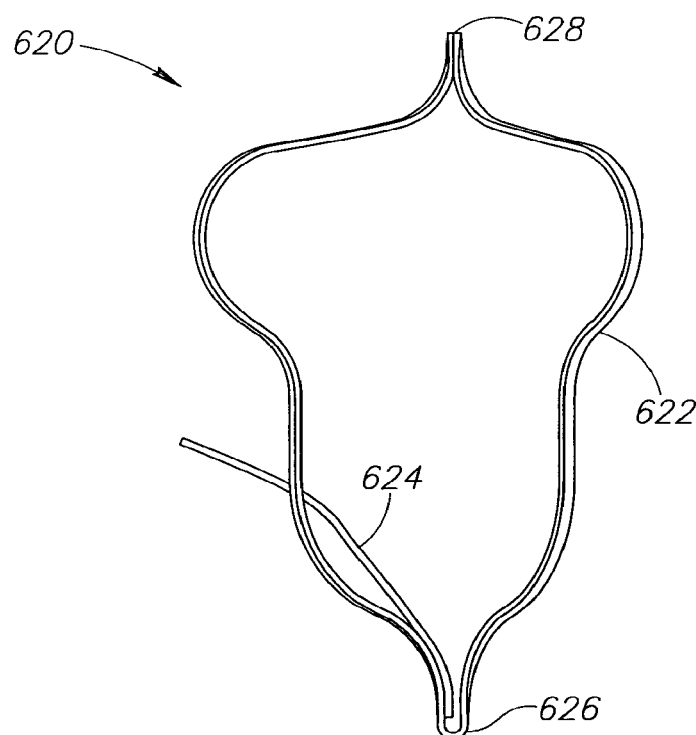
FIGS. 16A to 16D are schematic illustrations of a redial cutter implant, constructed and operative in accordance with a further embodiment of the disclosed technique.
Figure 16B:
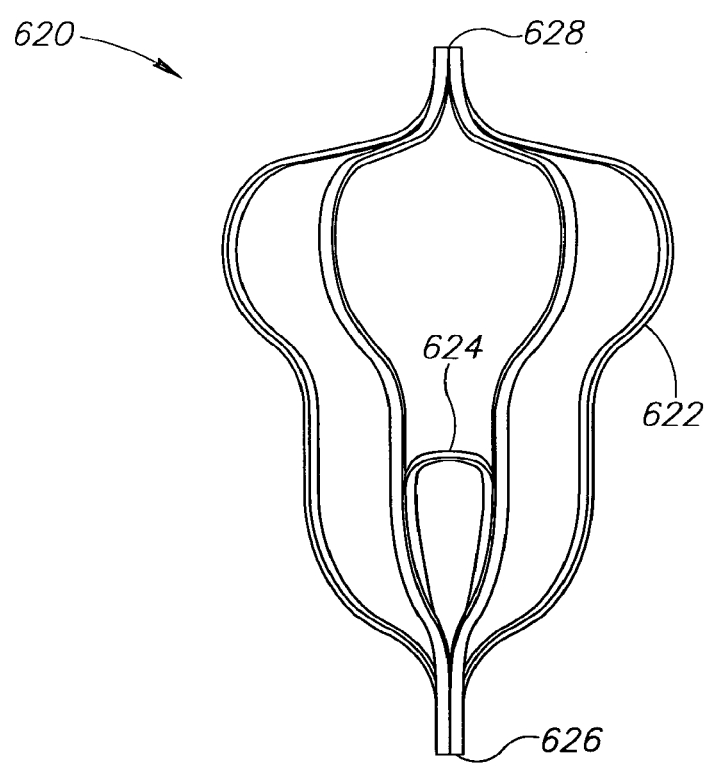
Figure 16C:
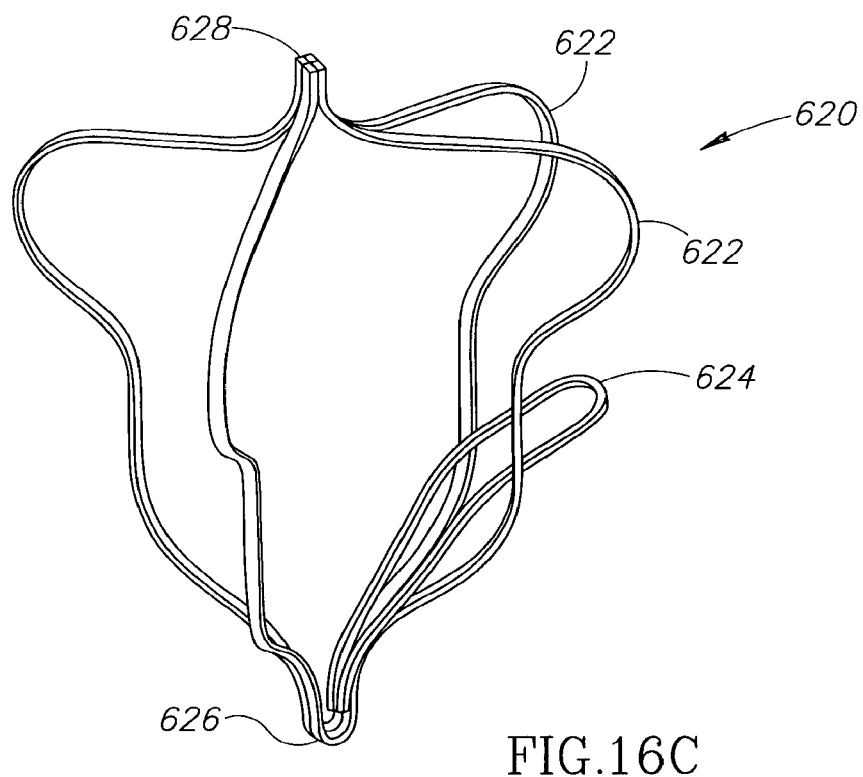
Figure 16D:
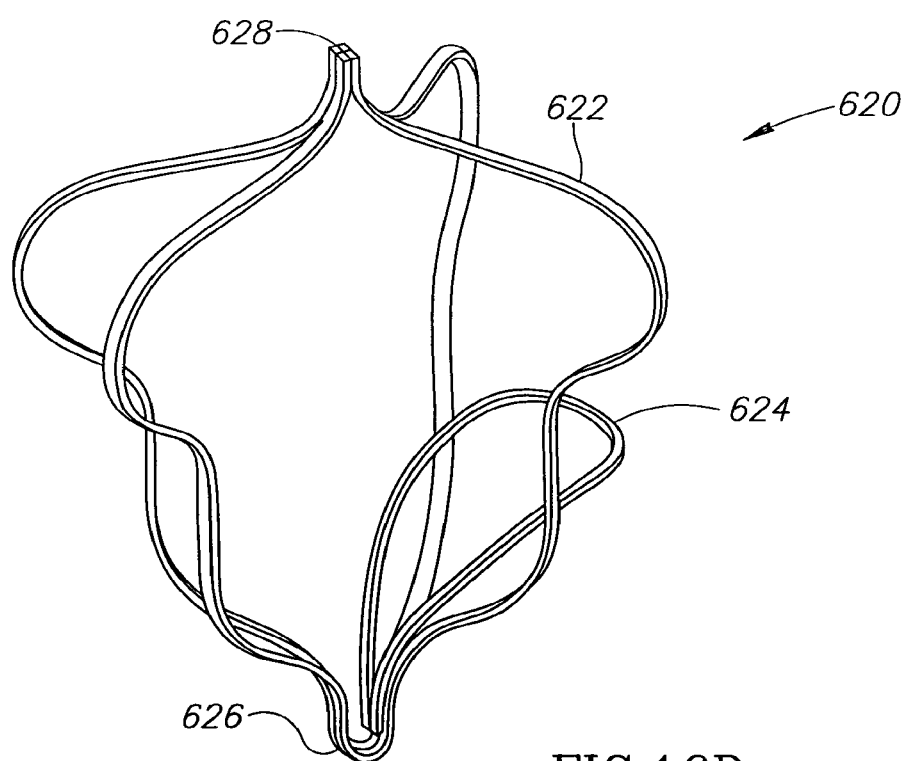

Reference is now made to FIGS. 13A, 13B and 13C, which are schematic illustrations of a radial cutter implant, generally referenced 520, constructed and operative in accordance with another embodiment of the disclosed technique. With reference to FIG. 13A, radial cutter implant 520 is depicted from a side view perspective. Radial cutter implant 520 is substantially similar to radial cutter implant 440 of FIG. 10A. Radial cutter implant 520 includes a tube 522 and three wires 524, 526 and 528. Each of wires 524, 526 and 528 includes two barbs 530. Tube 522 is a catheter which allows urine to pass there-through. Each of barbs 530 penetrates into the surrounding tissues (i.e., the tissues surrounding implant 520) for anchoring radial cutter implant 520 in place (i.e., for preventing migration of radial cutter implant 520 into the bladder or into the urethra). When radial cutter implant 520 is extracted from the bladder neck (i.e., pulled back in the distal direction), barbs 530 are pulled out of the surrounding tissues. With reference to FIG. 13B, FIG. 13B depicts an enlarged view portion 532 of radial cutter implant 520. Each of barbs 530 is directed in the proximal direction for preventing radial cutter 520 from moving in the proximal direction, from the bladder neck into the bladder (i.e., keeping radial cutter implant 520 anchored in place). With reference to FIG. 13C, radial cutter implant 520 is depicted from a bottom view perspective.

It is noted that, the number of wires including barbs can vary. Furthermore, the number of barbs on a wire can vary. For example, a radial cutter implant including five wires, three of which includes two barbs each, a fourth wire includes four barbs, and the fifth wire includes no barbs.

Reference is now made to FIG. 14, which is a schematic illustration of radial cutter implant, generally referenced 550, constructed and operative in accordance with a further embodiment of the disclosed technique. Radial cutter implant 550 includes a distal end 552 and two wires 554 and 556. Radial cutter implant 550 is substantially similar to radial cutter implant 350 of FIG. 7A, except for the number of wires (radial cutter implant 350 includes three wires and radial cutter implant 550 includes two wires). Each of wires 554 and 556 includes two barbs 558 and 560. The direction of extension of barbs 558 is different from the direction of extension of barbs 560 for enabling a stronger fixation into the bladder neck (i.e., stronger than a configuration of similar extending barbs).

Reference is now made to FIGS. 15A and 15B, which are schematic illustrations of a radial cutter implant, generally referenced 580, constructed and operative in accordance with another embodiment of the disclosed technique. With reference to FIG. 15A, radial cutter implant 580 is depicted from an isometric perspective. Radial cutter implant includes a tube 582, three wires 584, 586 and 588, and three wings 590, 592 and 594. Each of wires 584, 586 and 588 includes two barbs 596. Each of wires 584, 586 and 588 is coupled with the distal end of tube 582. Each of wings 590, 592 and 594 is coupled between tube 582 and each of wires 584, 586 and 588, respectively.

Each of wires 584, 586 and 588, and each of wings 590, 592 and 594 is flexible for enabling radial cutter implant 580 to be folded within an implant sheath (e.g., implant sheath 202 of FIG. 4A). Each of barbs 596 is substantially similar to each of barbs 558 of FIG. 14. While radial cutter implant 580 is implanted within the patient, tissue can grow around each of wires 584, 586 and 588. Tissue growth around wires 584, 586 and 588 complicates the extraction of radial cutter implant 580 and prevent the widening effect of implant 580. Wings 590, 592 and 594 prevent tissue from growing around wires 584, 586 and 588 and from holding radial cutter implant 580 in place. Wings 590, 592 and 594 are made from Polyester (PET), Poly-Urethane (PU), Nitinol foil, Silicon, and the like.

Reference is now made to FIGS. 16A to 16D, which are schematic illustrations of a redial cutter implant, generally referenced 620, constructed and operative in accordance with a further embodiment of the disclosed technique. Implant 620 includes four wires 622, an anchoring leaflet 624, a distal end 626 and a proximal end 628. Each of wires 622 is coupled between proximal end 628 and distal end 626. Anchoring leaflet 624 extends from distal end 626, and is positioned between two of wires 622.

Each of wires 622 is substantially similar to each of wires 474, 476, 478 and 480, all of FIG. 14A. The shape of wires 622 is wider at the proximal end than at the distal end thereof. In this manner, wires 622 prevent implant 620 from moving from the bladder neck into the urethra. In particular, the wider proximal portion of wires 622 is positioned within the bladder and the narrower distal portion of wires 622 is positioned at the bladder neck and within the urethra. Wires 622 (i.e., the wider proximal portion thereof) prevent implant 620 from moving out of the bladder and into the urethra by being blocked at the bladder neck.

Anchoring leaflet 624 is constructed of similar materials to those of wires 622. Anchoring leaflet 624 is in the shape of a tongue extending substantially in the proximal-normal direction (i.e., the normal direction refers to a direction normal to the proximal-distal axis—e.g., the dorsal direction). In this manner, anchoring leaflet 624 prevents implant 620 from moving from the bladder neck into the bladder. In particular, anchoring leaflet 624 is blocked by the bladder neck such that implant 620 can not move into the bladder. It is noted that, anchoring leaflet 624 can be a wire leaflet (e.g., as depicted in FIGS. 6A to 6D) or a full surface leaflet (e.g., substantially similar to wings 590 of FIG. 15A).

Alternatively, anchoring leaflet 624, extends in the distal-normal direction and prevents radial cutter implant 620 from moving in the distal direction towards the urethra. Further alternatively, there are at least two leaflets 624 extending in both directions and fixing implant 620 in place.

It is noted that, wires 622, and in particular the wider proximal portion thereof, prevent implant 620 from moving in the distal direction. Anchoring leaflet 624 prevent implant 620 from moving in the proximal direction. Thus, implant 620 is anchored in position within the bladder neck. It is further noted that, wires 622 and anchoring leaflet 624 are delivered within a sheath (e.g., implant sheath 202 of FIGS. 4A to 4C) and are expanded (e.g., self expand upon exposure from the sheath) once positioned in the bladder neck. The number of wire 622 of implant 620 is at least one, and can vary. The number of anchoring leaflets 624, is at least one and can vary.

Figure 17:
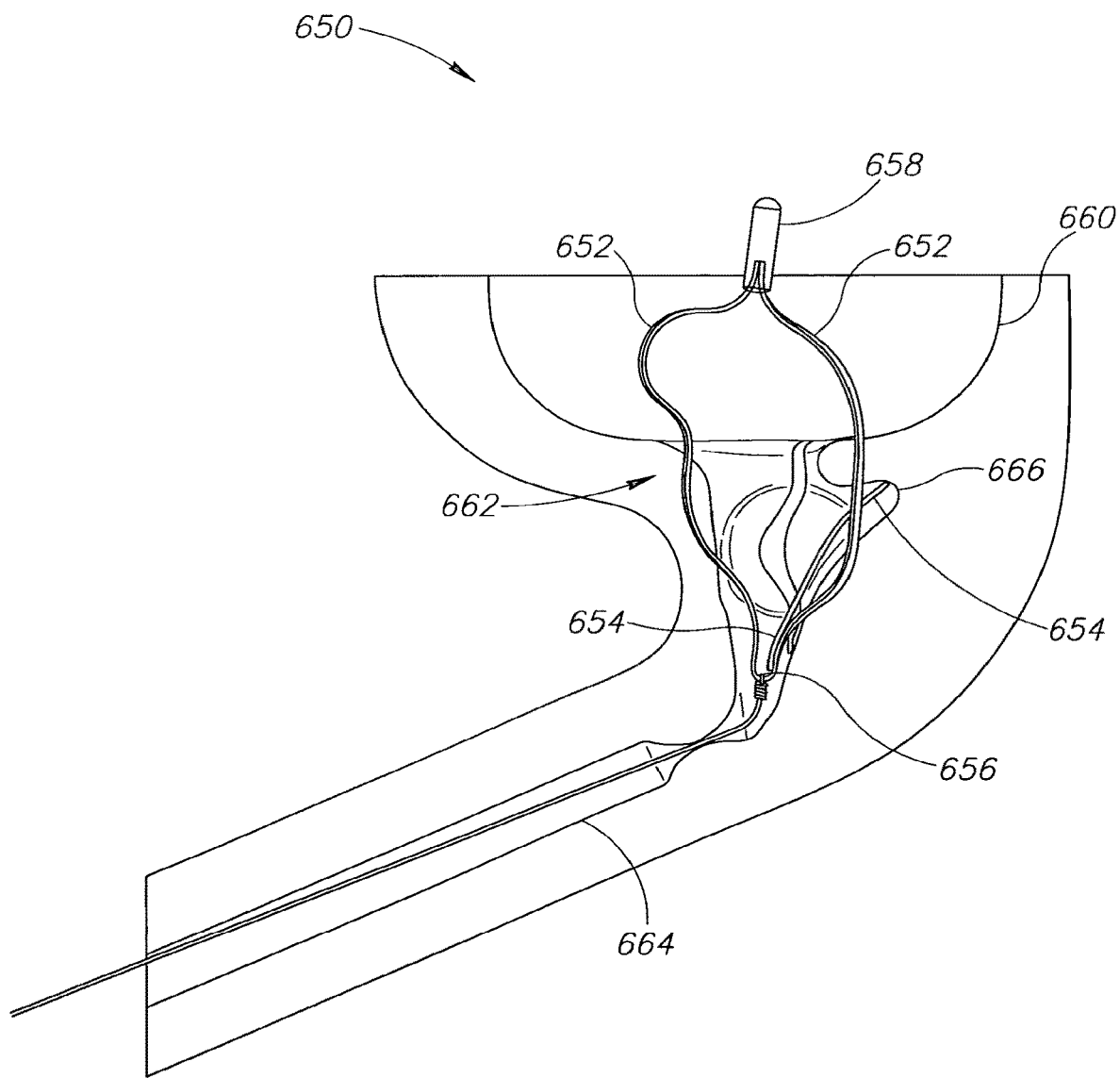
FIG. 17 is a schematic illustration of a redial cutter implant, positioned within a bladder neck of a patient, constructed and operative in accordance with another embodiment of the disclosed technique.

Reference is now made to FIG. 17, which is a schematic illustration of a redial cutter implant, generally referenced 650, positioned within a bladder neck of a patient, constructed and operative in accordance with another embodiment of the disclosed technique. Radial cutter implant 650 includes two wires 652, an anchoring leaflet 654, a distal end 656 and a proximal end 658. Radial cutter implant 620 is substantially similar to implant 620 of FIGS. 16A to 16D.

The distal wider portion of wires 652 is positioned within a bladder 660 of a patient (not shown). The proximal narrower portion of wires 652 is positioned within a bladder neck 662 of the patient. Anchoring leaflet 654 applies a proximal radial force against bladder neck 662 thereby producing a niche 666 within bladder neck 662. Anchoring leaflet 654 is anchored within niche 666. In this manner anchoring leaflet 654 anchors implant 650 within bladder neck 662. In other words, the proximal wider portion of wires 652 prevents implant 650 from moving distally (i.e., towards a urethra 664 of the patient) and anchoring leaflet 654 prevents implant 650 from moving proximally (i.e., towards bladder 660).

Alternatively, proximal end 658 is a substance release element, which slowly releases substances into the bladder neck, urethra and prostate of the patient, over a period of time. The released substances can include painkillers, anti-inflammatory materials, anti-biotic materials, and the like. Further alternatively, implant 620 (i.e., or at least some portions thereof, such as wires 652) is covered with such materials as detailed herein above, and releases these materials slowly into the body of the patient.

Figure 18:
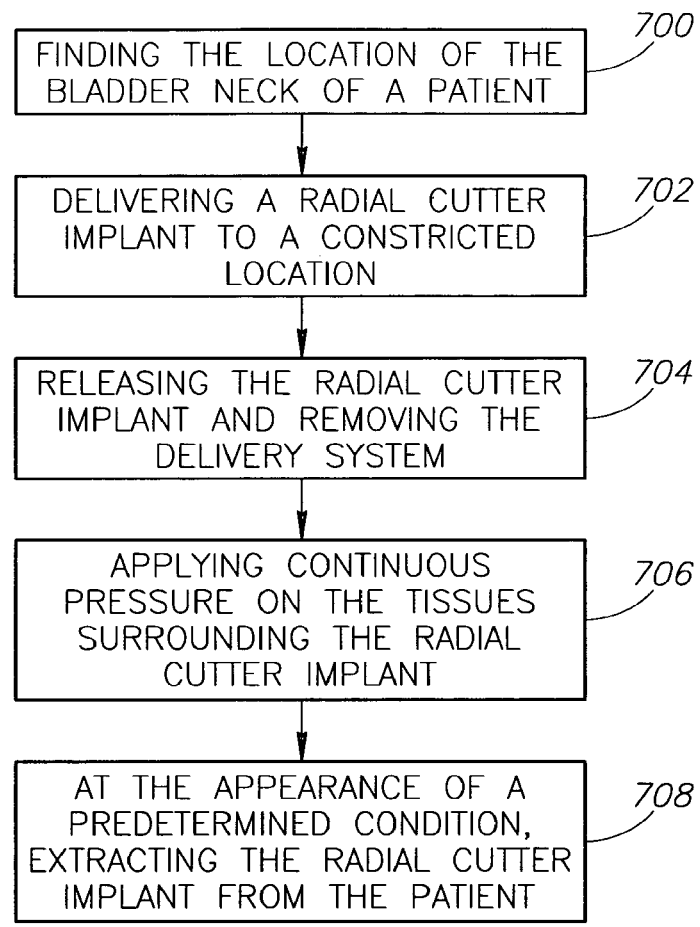
FIG. 18 is a schematic illustration of a method for creating incisions in the muscles of the bladder neck by infarction, operative in accordance with a further embodiment of the disclosed technique.

Reference is now made to FIG. 18, which is a schematic illustration of a method for creating incisions in the muscles of the bladder neck by infarction, operative in accordance with a further embodiment of the disclosed technique. In procedure 700, the location of the bladder neck of a patient is found. With reference to FIG. 3A, the physician inserts overtube 164 into the urethra of the patient until balloon 158 is inside bladder 152. The physician inflates balloon 158 and pulls overtube 164 back until balloon 158 is blocked by the bladder neck.

In procedure 702, a radial cutter implant is delivered to the constricted location. With reference to FIG. 3B, the physician inserts delivery 176 into positioning tube 162 and delivers radial cutter implant 178 to the location of the bladder neck (i.e., the constricted location). Alternatively, the physician delivers the implant to a different constricted location within the urinal system of the patient for relieving the constriction. In procedure 704, the radial cutter implant is released and the delivery system is removed. With reference to FIG. 3C, the physician exposes radial cutter implant 178 from implant sheath 166. Radial cutter implant 178 expands and attaches itself to the surrounding tissues (i.e., the wires of Radial cutter implant 178 are attached to the tissues surrounding the implant and apply pressure thereon). The physician removes delivery system 150 from urethra 154 of the patient.

In procedure 706, continuous pressure is applied on the tissues surrounding the implant by employing the radial cutter implant. With reference to FIG. 3C, the wires of radial cutter implant 178 apply continuous pressure on the surrounding tissues. In procedure 708, at the appearance of a predetermined condition, the radial cutter implant is extracted from the patient. With reference to FIG. 3C, the physician extracts radial cutter implant 178 from the patient at the appearance of a predetermined condition. The predetermined condition can be the passage of a predetermined period of time, the appearance of desired incisions on the surrounding tissues, the appearance of a predetermined physiological effect, and the like.

It will be appreciated by persons skilled in the art that the disclosed technique is not limited to what has been particularly shown and described hereinabove. Rather the scope of the disclosed technique is defined only by the claims, which follow.

The invention claimed is:

1. A method for expanding a constricted location of a urethra of a subject, the method comprising:
    inserting a urethral implant, and an implant sheath that covers said urethral implant, through said urethra for implanting said urethral implant in said constricted location, said urethral implant being in a compressed configuration within said implant sheath;
    releasing said urethral implant from said implant sheath until said urethral implant exits from said implant sheath, thereby expanding said urethral implant from said compressed configuration to an expanded configuration;
    applying, by said urethral implant, continuous pressure on tissues of said urethra at said constricted location; and
    retracting said implant sheath from said urethra;
    wherein said urethral implant comprises a proximal end, a distal end, and four wires extending between said proximal end and said distal end, and creating incisions in said tissues of said urethra at said constricted location, wherein a shape of the wires is a polygon.

2. The method according to claim 1, wherein said constricted location is at least one of a bladder neck and a prostatic urethra of said subject.

3. The method according to claim 2, further comprising: finding a location of at least one of said bladder neck and said prostatic urethra, performed before implanting said urethral implant.

4. The method according to claim 1, further comprising: employing a positioning tube for positioning said urethral implant at said constricted location.

5. The method according to claim 1, further comprising leaving said urethral implant implanted within said subject for a period of time between one hour and twenty nine days.

6. The method according to claim 1, further comprising: coupling said urethral implant with a proximal end of an internal tube, in said compressed configuration.

7. The method according to claim 6, further comprising: coupling said implant sheath with a proximal end of an external tube.

8. The method according to claim 7, further comprising: slidably coupling said internal tube with said external tube.

9. The method according to claim 8, further comprising: pulling said external tube while keeping said internal tube in place, such that said external tube slides along said internal tube in a distal direction of said urethral implant, to remove said implant sheath from said urethral implant.

10. The method according to claim 1, wherein said urethral implant is self-expanding.

\* \* \* \* \*